United States Patent
Bentolila et al.

(10) Patent No.: US 7,135,872 B2
(45) Date of Patent: Nov. 14, 2006

(54) METHOD OF DETERMINING THE COMPOSITION OF A MULTIPHASE FLUID

(75) Inventors: Yohan Bentolila, Paris (FR); Michel Constant, Montmorency (FR)

(73) Assignee: Institut Francais du Petrole, Rueil Malmaison Cedex (FR)

( * ) Notice: Subject to any disclaimer, the term of this patent is extended or adjusted under 35 U.S.C. 154(b) by 0 days.

(21) Appl. No.: 11/305,095

(22) Filed: Dec. 19, 2005

(65) Prior Publication Data

US 2006/0145709 A1 Jul. 6, 2006

(30) Foreign Application Priority Data

Dec. 23, 2004 (FR) .................................. 04 13804

(51) Int. Cl.
 G01R 27/32 (2006.01)
 G01N 9/24 (2006.01)
 G01F 25/00 (2006.01)

(52) U.S. Cl. .................... 324/640; 324/717; 73/61.44; 702/100

(58) Field of Classification Search ............... 324/717, 324/639–640; 73/61.44; 702/100
See application file for complete search history.

(56) References Cited

U.S. PATENT DOCUMENTS

| 4,902,961 A | 2/1990 | De et al. |
|---|---|---|
| 5,103,181 A * | 4/1992 | Gaisford et al. ............ 324/637 |
| 5,485,743 A * | 1/1996 | Taherian et al. ........... 73/61.44 |
| 5,625,293 A | 4/1997 | Marrelli et al. |
| 5,793,216 A * | 8/1998 | Constant ..................... 324/639 |
| 2002/0123852 A1* | 9/2002 | Gysling et al. ............. 702/100 |
| 2004/0210409 A1 | 10/2004 | Miljak |
| 2004/0225464 A1* | 11/2004 | Melbo et al. ............... 702/100 |
| 2004/0229376 A1 | 11/2004 | Beauducel et al. |

OTHER PUBLICATIONS

Ebbe Nyfors and Petrti Vainikainen: Industrial Microwave Sensors, 1989, Artech House, U.S., pp. 69–87, XP002338981, ISBN: 0-89006-397-4.

* cited by examiner

Primary Examiner—Anjan Deb
(74) Attorney, Agent, or Firm—Antonelli, Terry, Stout and Kraus, LLP.

(57) ABSTRACT

A method of determining the composition of a multiphase fluid, such as a flowing petroleum effluent, an emulsion of water and oil, or a foam of oil and gas is disclosed. A first part comprises determining a model expressing the attenuation and the phase shift of a microwave beam as a function of the volume fractions and the permittivities of the various phases. Then, a second part comprises determining the volume fractions of the various phases that make up a multiphase fluid by minimizing the distance between the measured attenuation and phase shift pair and the attenuation and phase shift pair given by the previously determined model.

32 Claims, 3 Drawing Sheets

METHOD OF DETERMINING THE COMPOSITION OF A MULTIPHASE FLUID

BACKGROUND OF THE INVENTION

1. Field of the Invention

The present invention relates to a method of determining the composition of a fluid. More precisely, the invention provides a data processing method analyzing characteristics of microwave beams that have traversed a fluid in order to determine the composition of this fluid.

2. Description of the Prior Art

French Patent 2,833,705 discloses a separator drum comprising a first rod provided with microwave beam emitters and a second rod provided with microwave beam receivers. The separator contains a petroleum effluent from a production well. A microwave source is connected to the emitters so that each emitter can emit a microwave beam. An acquisition device records the microwave beams picked up by the receivers, as well as the microwave beam emitted by the source.

SUMMARY OF THE INVENTION

In general terms, the present invention relates to a method of determining the composition of a multiphase fluid comprising at least two mixed phases, wherein the following stages are carried out:

a) selecting a mixture law that expresses the mean permitivity of the fluid as a function of the permitivity and the volume fraction of each phase;

b) measuring attenuation and phase shift of at least two microwave beams of different frequencies that have traversed test fluids of known composition;

c) from the mixture law and from the attenuation and phase shift measurements performed in b), determining for each one of the frequencies a measurement model that expresses the attenuation and the phase shift of a microwave beam as a function of the volume fraction of each phase;

d) for each one of the frequencies, measuring an attenuation and phase shift pair for at least one microwave beam that has traversed said multiphase fluid;

e) determining the composition of the multiphase fluid by determining the value of the volume fractions of the phases that minimize a function taking into account of distances, calculated for each one of the frequencies, between a point whose coordinates correspond to the attenuation and phase shift pair measured for a value of the frequencies and a point whose coordinates correspond to the attenuation and the phase shift pair determined by one of the models valid for the same frequency value.

According to the invention, in e), the function can correspond to the sum of the distances.

The method according to the invention is particularly well suited for determining the composition of a homogeneous multiphase fluid comprising for example water, oil and/or gas. For example, the method can be applied for determination of the composition of a petroleum effluent contained in a separator drum or circulating in a pipe.

The present invention provides a method of processing characteristics of the microwave beams picked up by the receivers in order to determine the composition of the fluid traversed by these beams.

In the method according to the invention, in e), the value of the volume fractions that minimize the sum of the at least two following distances can be determined: the distance between the attenuation and the phase shift pair measured for a first one of the frequencies and the attenuation and phase shift pair determined by one of the valid models for the first one of the frequencies, and the distance between the attenuation and phase shift pair measured for a second one of the frequencies and the attenuation and phase shift pair determined by another one of the valid models for the second one of the frequencies.

According to the invention, the fluid can be a petroleum effluent comprising water, oil and gas. In this case, in c), it is possible to determine a first measurement model expressing the attenuation and the phase shift of a microwave beam as a function of the volume fraction of the water and it is possible to determine a second measurement model expressing the attenuation and the phase shift of a microwave beam as a function of the volume fraction of the gas. In e), it is possible to determine the value of the volume fraction of the water that minimizes the sums, on frequencies, of the distances between the measured attenuation and phase shift pair and the attenuation and phase shift pair determined by the first model, and it is possible to determine the value of the volume fraction of the gas that minimizes the sums, on the frequencies, of the distances between the measured attenuation and phase shift pair and the attenuation and phase shift pair determined by the second model.

According to the invention, in a), the mixture law can be selected from among the Bruggeman-Hanaï law, the Tinga-Voss-Blossey law and a law given by the CRIM method. For example, the first model is determined from the Bruggeman-Hanaï law and the second model is determined from a law given by the CRIM method.

According to the invention, before a), it is possible to determine the permitivity values of the phases and to use the permitivity values in a).

According to the invention, in stage b), microwave beams of frequencies in the range from 2 GHz to 10 GHz can be used.

In b), several attenuation and phase shift measurements can be performed at a microwave frequency and a mean of the measurements can be worked out.

The fluid can be a petroleum effluent of gas, oil and water.

BRIEF DESCRIPTION OF THE DRAWINGS

Other features and advantages of the invention will be clear from reading the description hereafter given by way of example, with reference to the accompanying figures wherein.

DETAILED DESCRIPTION OF THE INVENTION

Figure 1:
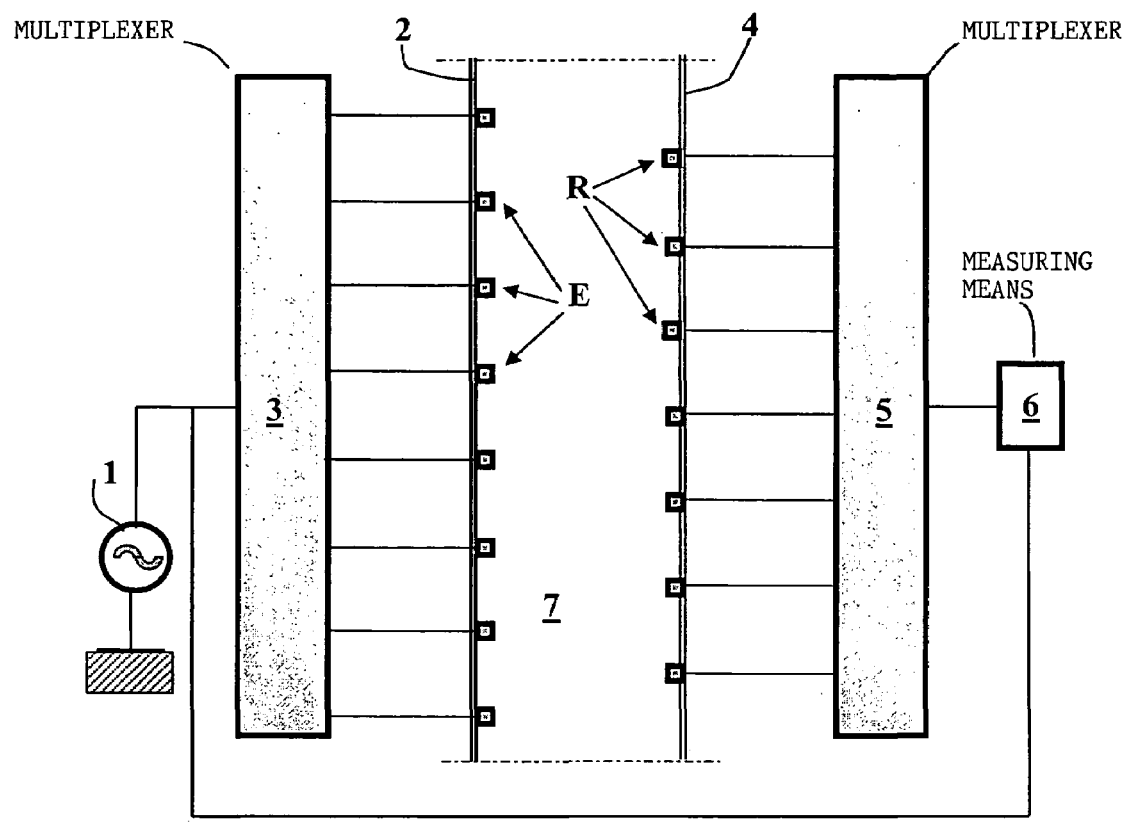
FIG. 1 diagrammatically shows the measuring device.

The method according to the invention can use the measurements obtained by means of the measuring device diagrammatically shown in FIG. 1. The measuring device comprises a microwave beam source 1 connected to microwave emitters E arranged on first line 2. The frequency of the microwave beam emitted by source 1 can be selected and modified. Microwave beam receivers R arranged on second line 4 are connected to measuring means 6. A fluid 7 whose composition is to be determined, a petroleum effluent for example, is in position in the space located between first line 2 and second line 4. A multiplexer 3 allows connection of source 1 to any one of emitters E. Thus, the emitter that is connected to source 1 emits a microwave beam that is propagated in fluid 7. The microwave beams are considered to be propagated along straight lines in fluid 7. Multiplexer 5 allows connection of any one of receivers R to measuring means 6. Measuring means 6 are also connected to source 1. Thus, measuring means 6 can record both the characteristics of the microwave beam picked up by the receiver that is connected to measuring means 6 and the characteristics of the microwave beam directly emitted by source 1.

The emitters and receivers can be on first and second lines 2 and 4 so as to have one or more emitter-receiver pairs separated by the same distance.

Lines 2 and 4 can be in form of curves, of parallel or non-parallel lines. The emitters can be arranged at regular intervals on first line 2 (that is the value of the distance between two adjacent emitters is identical for all the emitters) and/or the receivers can be arranged at regular intervals on second line 4 (that is the value of the distance between two adjacent receivers is identical for all the receivers). When the emitters and the receivers are arranged at regular intervals on lines 2 and 4, the value of the interval between two adjacent emitters can be equal to or be a whole multiple of the value of the interval between two adjacent receivers.

Lines 2 and 4 can be located on the walls of an enclosure containing fluid 7, for example the wall of a pipe in which fluid 7 circulates. Lines 2 and 4 can also be located on rods that dip in fluid 7 contained in an enclosure, for example in a separator drum used in the petroleum industry.

Emitters E and receivers R are antennas known to in the art, for example described in connection with FIG. 2 of French Patent 2,833,705.

Without departing from the scope of the invention, the type of wave produced by source 1 can also be selected from among electromagnetic radiation waves such as microwaves, the infrared, nuclear radiation, optical light, or from acoustic waves such as ultrasounds.

Fluid 7 can be a single-phase fluid, that is one or more constituents that mix. Fluid 7 can also be a multiphase fluid, that is several constituents that do not mix. The method according to the invention is suited for determining the composition of a mixed multiphase fluid, i.e. a fluid whose composition is substantially identical in any part of the fluid or, in other words, the constituents of the fluid are distributed in a substantially identical manner throughout the fluid.

For example, fluid 7 can be a petroleum effluent comprising water, oil and/or gas.

Figure 2:
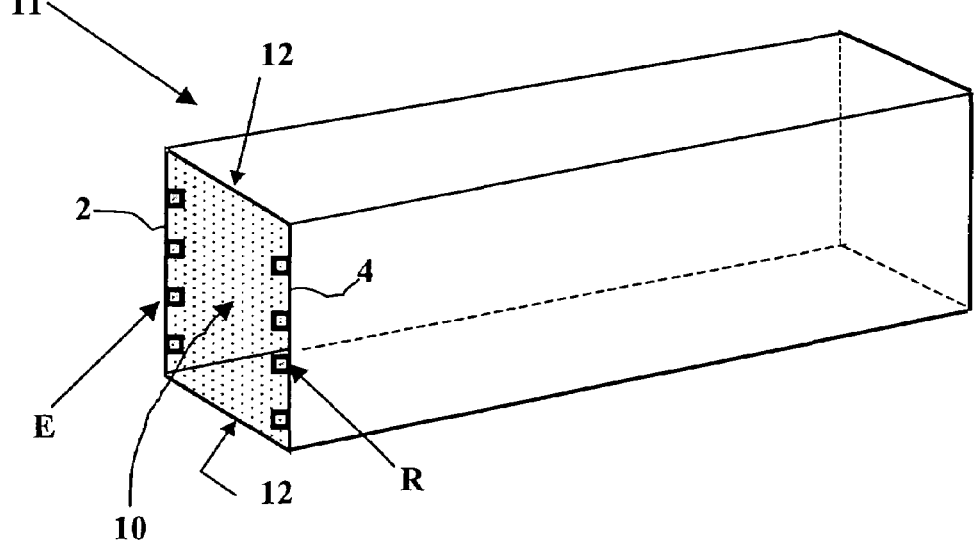
FIGS. 2 and 3 show two examples of fluids to which the method according to the invention can be applied

In connection with FIG. 2, petroleum effluent 10 can be on turbulent flow in a pipe 11. In this case, the composition of the effluent can be homogeneous that is the water, the oil and the gas are evenly distributed throughout pipe 11. In this case, the method allows to determine the water, oil and gas content of the effluent.

Figure 3:
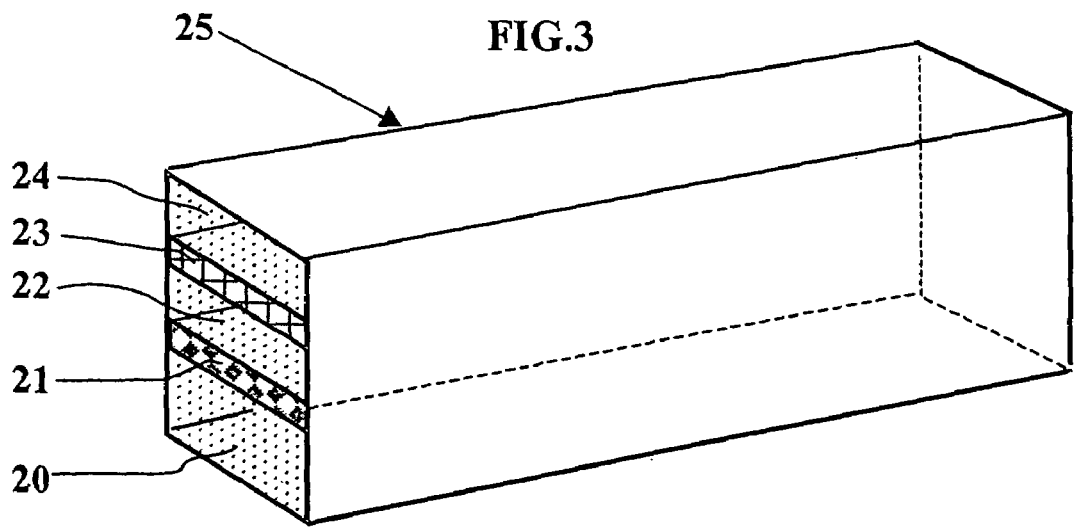

According to another option diagrammatically shown in FIG. 3, water 20, oil 22 and gas 24 can be distributed in form of stratified layers, for example when the effluent is on laminar flow in a pipe 25 or when the effluent settles in a separator drum. More precisely, the effluent comes in form of superposed layers: a water layer 20, a water/oil emulsion layer 21, an oil layer 22, an oil/gas foam layer 23 and a gas layer 24. In this case, the method notably allows determination of the proportions of water and oil making up emulsion layer 21, and the proportions of oil and gas making up foam layer 23. To determine the composition of the emulsion (respectively of the foam), only the microwave beams that have travelled a path located only in emulsion layer 21 (respectively in foam layer 23) are taken into account.

The measuring device described in connection with FIG. 1 operates by double emission and reception multiplexing. Microwave source 1 produces a microwave beam of selected frequency f1. Multiplexer 3 connects microwave source 1 successively to each emitter E. Thus, the emitters emit one after the other a microwave beam. During the time of emission of one emitter E, multiplexer 5 connects successively or simultaneously each receiver R to measuring means 6. Measuring means 6 also measure the microwave beam emitted by source 1. Thus, measuring means 6 measure the characteristics of the microwave beam emitted by an emitter and picked up by each receiver. It is thus possible to measure the microwave beam emitted by an emitter and picked up by a receiver, for all the emitter-receiver pairs available.

Frequency f1 can be selected in such a way that the microwave beam is substantially modified by at least one of the constituents of fluid 7 when the beam is propagated in fluid 7, that is the attenuation and the phase shift are noticeable when the beam is propagated in fluid 7. For example, frequency f1 is so selected that the microwave beam is substantially modified when it traverses natural gas ($CH_4$). Thus, by measuring the attenuation and the phase shift of a beam of frequency f1 that has traversed a petroleum effluent, information on the natural gas content of this effluent is obtained.

The measurements can be repeated for several microwave beam frequencies. The frequencies can be selected in such a way that, for each frequency, the microwave beam is substantially modified by a different constituent. For a petroleum fluid containing water, oil and/or gas, the frequencies can be selected between 1 GHz and 100 GHz, preferably between 2 GHz and 10 GHz, for example the four frequencies included in the following ranges:

fa from 2 GHz to 2.7 GHz
fb from 2.7 GHz to 3.7 GHz
fc from 3.7 GHz to 6 GHz
fd from 6 GHz to 10 GHz The method according to the invention analyzes the phase shift and the attenuation of a microwave beam that has traversed the fluid in order to determine the composition of this fluid.

The attenuation and the phase shift of the beam that has traversed the fluid over the distance between an emitter E and a receiver R can be determined knowing the characteristics of the microwave beam emitted by this emitter (that is the beam emitted by source 1) and the characteristics of the microwave beam picked up by this receiver.

The characteristics of a single beam emitted by an emitter E and received by only one receiver can be used to determine the attenuation and the phase shift of a beam that has travelled a known distance in a fluid.

In order to obtain more reliable attenuation and phase shift values, the mean of the measured attenuations and phase shifts corresponding to beams that have travelled paths of equal distance in the fluid can be worked out. Thus, a mean attenuation and phase shift value is obtained, which limits taking account of phenomena that may occur in isolation during measurement and distort the result. A single phase shift and attenuation value corresponding to the beams that have travelled a determined distance is obtained.

Preferably, the values corresponding to the beams that have travelled paths of shorter distance are used.

A weighted mean of the values can be worked out. It is thus possible for example to minimize the edge effects due notably to the reflection of the microwave beams and to variations in the inhomogeneity of fluid 7.

In fact, in connection with FIG. 2, emitters E and receivers R located at the ends of lines 2 and 4 can be close to walls 12 of the pipe or of the enclosure containing fluid 10. The structure of fluid 10 can be modified in the area surrounding walls 12, for example as a result of the flow of fluid 10 that is altered by the presence of walls 12. Thus, the attenuation and the phase shift of the microwave beams that traverse these fluid portions in the area around walls 12 are not representative of the entire structure of fluid 10.

Furthermore, microwave beams are reflected on walls 12 of the pipe or of the enclosure containing fluid 10. Receivers R arranged close to walls 12 can record these reflected beams. Thus, the attenuation and the phase shift determined from the microwave beam emitted by an emitter and the microwave beams measured by a receiver arranged close to a wall 12 may not be representative of the attenuation and the phase shift of the beam propagated rectilinearly from this emitter to this receiver.

Consequently, by working out a weighted mean of the measurements, a lesser weight can be given to the attenuation and phase shift values measured close to walls 12. Thus, these attenuation and phase shift values will be less important in relation to the other values during the subsequent stages of the method according to the invention.

Figure 4:
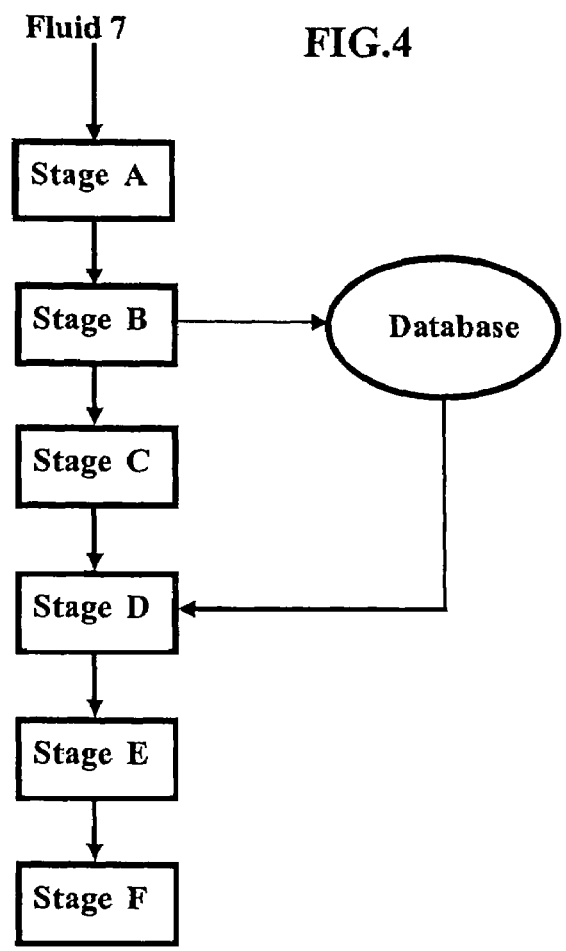
FIG. 4 shows a diagram of the method according to the invention.

The method according to the invention uses physical behavior laws modelling, on the one hand, the permittivity of a fluid resulting from mixing several phases of known permittivity and, on the other hand, the propagation of a microwave beam through a multiphase fluid to estimate the proportions of the various phases making up this fluid. The method described in connection with FIG. 4 is divided up in two parts: a first part wherein the physical behavior laws are calibrated and a second part wherein the proportions of the various phases making up the multiphase fluid are estimated using the previously calibrated physical behaviour laws.

The invention is described hereafter in its application to the estimation of the proportions of gas, oil and water in a petroleum fluid. However, without departing from the scope of the invention, the method according to the invention can be applied to the estimation of the proportions of the phases of another multiphase fluid.

First Part: Calibration of the Physical Behaviour Laws

During A, the permittivities of the various phases that make up the fluid studied are determined. In the case of a petroleum fluid, the permittivity of the gas, of the oil and of the water is determined.

For example, the permittivity of the phases is determined from attenuation and phase shift measurements and using a relation that gives the permittivity $\epsilon_m$ of the medium as a function of attenuation p and phase shift $\phi$.

Attenuation ρ and phase shift φ of the wave measured at the receiving antenna of the microwave detector located at a distance d from the incident wave can be defined by:

$$\rho = \rho_0 \exp(-ad)$$

$$\phi = bd$$

On the other hand, coefficients a and b are related to the complex permittivity of the medium by:

$$a = \frac{2\pi f}{c_0} |\text{Im}(\sqrt{\varepsilon_m})|$$

$$b = \frac{2\pi f}{c_0} |\text{Re}(\sqrt{\varepsilon_m})|$$

$c_0$ being the speed of light in vacuum, f being the frequency of the microwave beam.

Permittivity of the gas:

According to the invention, the permittivity of the gas is considered to be constant. This permittivity varies very little with the pressure, the temperature and the frequency of the microwaves.

The attenuation and the phase shift of a microwave beam traversing a medium consisting of 100% gas are measured.

The permittivity of the gas $\epsilon_{gas}$ is determined from this attenuation and phase shift measurement.

Permittivity of the oil:

According to the invention, the permittivity of the oil is considered to be constant. This permittivity varies very little with the pressure and the temperature.

The attenuation and the phase shift of a microwave beam traversing a medium consisting of 100% oil are measured.

The permittivity of the oil $\epsilon_{oil}$ is determined from this attenuation and phase shift measurement.

Permittivity of the water:

The permittivity of the water is sensitive to the temperature of the water, the salinity of the water and the microwave frequency.

The attenuation and the phase shift of a microwave beam of known frequency traversing a medium of 100% water having a given temperature and salinity are measured. The permittivity of the water $\epsilon_{water}$ at a given temperature and salinity is determined from this attenuation and phase shift measurement.

The microwave beam attenuation and phase shift measurements are repeated by varying the temperature and the salinity of the water, as well as the frequency of the microwave beam. The permittivity of the water $\epsilon_{water}$ is determined from these measurements for different temperature, salinity and microwave beam frequency values.

A set of values are obtained for the permittivity of the water as a function of the temperature and the salinity of the water, for various microwave beam frequencies, for example for frequencies fa, fb, fc and fd.

According to the invention, the permittivity values of the gas, the oil and the water can be normalized in relation to the permittivity of one of these phases. For example, the permittivity of the gas is arbitrarily set at 1, and the relative permittivities of the oil and of the water in relation to the permittivity of the gas, which is 1, are determined.

The table hereafter illustrates the apparent permittivity values according to the microwave beam frequencies, by normalizing these values in relation to the permittivity of the gas which is set at 1.

| Frequency in GHz | $\epsilon_{water}$ (apparent) | $\epsilon_{oil}$ (apparent) |
|---|---|---|
| fa | 81 + 6.9j | 3.5 + 2.3j |
| fb | 82.1 − 7.3j | 4.0 + 0.026j |
| fc | 75.3 − 11j | 2.7 + 0.3j |

In B, we select laws which, on the one hand, model the permittivity of a fluid resulting from mixing several phases of known permittivities and, on the other hand, express the physical behaviour of the attenuation and of the phase shift of a microwave beam traversing this medium.

For fluids in admixture, the "mixture laws" express the mean permittivity $\varepsilon_m$ of the medium as a function of the permittivity $\varepsilon$ and of the volume fraction $\alpha$ of each constituent of the mixture.

For example, the following mixture laws can be used:
The Bruggeman-Hanaï law:

$$\frac{\varepsilon_m - \varepsilon_i}{\varepsilon_h - \varepsilon_i}\left(\frac{\varepsilon_h}{\varepsilon_m}\right)^L = 1 - \alpha_i$$

L being a depolarization factor ranging between 0 and 1
$\varepsilon_h$ being the permittivity of the continuous or host medium,
$\varepsilon_i$ being the permittivity of the medium that exhibits inclusions in the continuous medium;
the Tinga-Voss-Blossey law:

$$\varepsilon_m = \varepsilon_h + \frac{1}{3}\sum_{i=1,2} p_i(\varepsilon_i - \varepsilon_h)\sum_{u=a,b,c}\frac{1}{1+A_u\left(\frac{\varepsilon_i}{\varepsilon_m}-1\right)}$$

$A_u$ being a form factor that ranges between 0 and 1;
the law given by the CRIM (Complex Refractive Index Method) method:

$$(\varepsilon_m)^c = \sum_{i=1,2,3} \alpha_i(\varepsilon_i)^c$$

c being a parameter ranging between −1 and 1
$\alpha_i$ and $\varepsilon_i$ being respectively the volume fraction and the permittivity of phase i.

A Bruggeman-Hanaï law or a law given by the CRIM method is preferably selected.

According to the invention, the following can be selected to determine a two-phase mixture:
a mixture law for a water/oil mixture $\varepsilon_m = F_{eh}(\varepsilon_{water}, \varepsilon_{oil}, \alpha_{water}, \alpha_{oil})$
a mixture law for a gas/water mixture $\varepsilon_m = F_{ge}(\varepsilon_{gas}, \varepsilon_{water}, \alpha_{gas}, \alpha_{water})$
a mixture law for a gas/oil mixture $\varepsilon_m = F_{gh}(\varepsilon_{gas}, \varepsilon_{oil}, \alpha_{gas}, \alpha_{oil})$.

For each mixture law, the attenuation and the phase shift are expressed as a function of the permittivity. For example, the relation mentioned in stage A can be used. Thus, the following measurement models are obtained:
a measurement model $z_{eh}$ for a water/oil mixture that expresses attenuation $\rho$ and phase shift $\phi$ as a function of the proportion of water $\alpha_e$, by taking into account the microwave beam frequency, in the form $(\rho, \phi) = z_{eh}(\alpha_e)$,
a measurement model $z_{ge}$ for a gas/water mixture that expresses attenuation $\rho$ and phase shift $\phi$ as a function of the proportion of gas $\alpha_g$, by accounting for the microwave beam frequency, in the form $(\rho, \phi) = z_{ge}(\alpha_g)$,
a measurement model $z_{gh}$ for a gas/oil mixture that expresses attenuation $\rho$ and phase shift $\phi$ as a function of the proportion of gas $\alpha_g$, in the form $(\rho, \phi) = z_{gh}(\alpha_g)$.

In C, the parameters of the physical laws are adjusted.

According to the invention, the parameters of each mixture law are adjusted using measurements of the attenuation and of the phase shift of the microwave beam that has traversed emulsion samples of known composition.

For example, the attenuation and the phase shift of a microwave beam of known frequency that has traversed water/oil mixtures of known compositions are measured. The measurements can be performed on mixtures, for example between two and six water/oil mixtures, whose water proportion ranges between 20% and 80% by volume. The temperature and the salinity of the water making up these mixtures are known, for example T=25° C. and salinity=0 g/l. Then, the parameters of the measurement model $(\rho, \phi) = z_{eh}(\alpha_e)$ are adjusted so that the measurement model best matches the attenuation and phase shift values measured on the water/oil mixtures of known composition.

This adjustment of the parameters of measurement model $z_{eh}$ is performed with attenuation and phase shift values measured for several microwave beam frequencies, for example for the three frequencies fa, fb and fc. Thus, several measurement models $z_{eh}$ are obtained, each model corresponding to one of the frequencies. If the three frequencies fa, fb and fc were selected, three measurement models $z_{eh}$ are obtained, respectively valid at frequencies fa, fb and fc.

Similarly, the parameters of measurement models $(\rho, \phi) = z_{ge}(\alpha_g)$ and $(\rho, \phi) = z_{gh}(\alpha_g)$ are adjusted using the attenuation $\rho$ and phase shift $\phi$ measurements obtained from mixtures of known composition and from known microwave beam frequencies.

The adjusted measurement models are thus obtained.

From the various measurement models, it is possible to construct a global two-phase model that expresses the attenuation $\rho$ and the phase shift $\phi$
measured at a known microwave frequency, as a function of the proportion of water and of gas.

$$(\rho, \varphi) = z_G(\alpha_e, \alpha_g) = \begin{cases} z_{eh}(\alpha_e) & \text{if } \alpha_g = 0 \\ z_{gh}(\alpha_g) & \text{if } \alpha_e = 0 \\ z_{eg}(\alpha_g) & \text{if } \alpha_g + \alpha_e = 1 \end{cases}$$

Preferably, several global two-phase models are constructed, one model being valid for one microwave beam frequency. For example, three global two-phase models are constructed, the first model being valid for frequency fa, the second model being valid for frequency fb and the third model being valid for frequency fc.

Alternatively, in B, for a three-phase mixture of water, oil and gas, the two-phase laws can be generalized to a mixture of more than two phases by considering that the host medium (or continuous medium) of two phases whose volume fraction ratio is constant. In this case, we can select:

a mixture law $\varepsilon_m = F_{eh}(\varepsilon_{water}, \varepsilon_{GOR}, \alpha_{water}, \alpha_{GOR})$ $F_{eh}$ being a mixture law for a water/oil mixture, $$\alpha_{GOR} = \frac{\alpha_g}{\alpha_h + \alpha_g} \text{ is constant,}$$

$\varepsilon_{GOR} = F_{gh}(\varepsilon_{gas}, \varepsilon_{oil}, \alpha_{GOR})$, $F_{gh}$ being a gas/oil mixture law.

a mixture law $\varepsilon_m = F_{gh}(\varepsilon_{gas}, \varepsilon_{WC}, \alpha_{gas}, \alpha_{WC})$ $F_{gh}$ being a gas/oil mixture law.

$$\alpha_{WC} = \frac{\alpha_e}{\alpha_h + \alpha_e} \text{ is constant,}$$

$\epsilon_{WC} = F_{eh}(\epsilon_{water}, \epsilon_{oil}, \alpha_{WC})$ $F_{eh}$ being a mixture law for a water/oil mixture.

Then, as above, for each mixture law, the attenuation and the phase shift are expressed as a function of the permittivity.

Then C is carried out: the parameters of the physical behavior laws are adjusted using the attenuation $\rho$ and phase shift $\phi$ measurements obtained from mixtures of known composition, and the following models are determined:

a measurement model $z_{GOR}$ for a water/oil/gas mixture that expresses attenuation $\rho$ and phase shift $\phi$ as a function of the proportion of water $\alpha_e$, by taking into account the microwave beam frequency, in the form $(\rho,\phi)=z_{GOR}(\alpha_e)$, a measurement model $z_{wc}$ for a water/oil/gas mixture that expresses attenuation $\rho$ and phase shift $\phi$ as a function of the proportion of gas $\alpha_g$, in the form $(\rho,\phi)=z_{wc}(\alpha_g)$.

Alternatively, in B, according to the invention, a mixture law $\epsilon_m = F_{ghe}(\epsilon_{gas}, \epsilon_{oil}, \epsilon_{water}, \alpha_{gas}, \alpha_{oil}, \alpha_{water})$ can be directly used for a multiphase fluid consisting of water, oil and gas.

B is then carried out by adjusting the parameters of mixture law $F_{ghe}$ using attenuation and phase shift measurements of microwave beams that have traversed fluid samples of known composition.

For example, the attenuation and the phase shift of microwave beams of known frequency that have traversed gas/oil/water mixtures of known composition are measured. The measurements can be performed on fluids, for example between three and twelve gas/oil/water mixtures, whose gas, water and oil proportions range between 20% and 80% by volume. The temperature and the salinity of the water making up these mixtures are known, for example T=25° C. and salinity=0 g/l. Then the parameters of measurement model $(\rho,\phi)=z_G(\alpha_e, \alpha_g)$ are adjusted in such a way that the measurement model best matches the attenuation and phase shift values measured on the water/oil/gas mixtures of known composition.

This adjustment of the parameters of measurement model $z_G$ is carried out with attenuation and phase shift values measured for several microwave beam frequencies, for example for the three frequencies fa, fb and fc. Thus, several measurement models $z_G$ are obtained, each model corresponding to one of the frequencies. If the three frequencies fa, fb and fc were selected, three measurement models $z_G$ respectively valid at frequencies fa, fb and fc are obtained.

Second Part: Estimation of the Proportions of the Various Phases Making Up an Emulsion In D, a fluid the proportions of the various phases of which are to be estimated is fed into the measuring device, for example the device described in connection with FIG. 1.

The temperature and the salinity of the fluid are measured.

In the measurement models determined in the first part (calibration), the water permittivity value (in our example, the permittivity of the water was used at T=25° C. and salinity=0 g/l) is replaced by the water permittivity value corresponding to the temperature and to the salinity of the fluid studied, this value being taken in the database relative to the water permittivity as a function of the temperature and the salinity, and constructed in the first part (calibration).

The suitable measurement models $(\rho,\phi)=z_G(\alpha_e, \alpha_g)$ according to the temperature and the salinity of the fluid studied are obtained.

In E, an attenuation and phase shift pair z is measured for microwave beams that have traversed the fluid studied. Several attenuation and phase shift measurements are performed on microwave beams having different frequencies. For example, three attenuation and phase shift pairs z are measured using three different microwave beams of frequency fa, fb and fc.

Besides, the attenuation and the phase shift are expressed using measurement model $z_G$ corresponding to the frequency of the microwave beams used during measurement.

Figure 5:
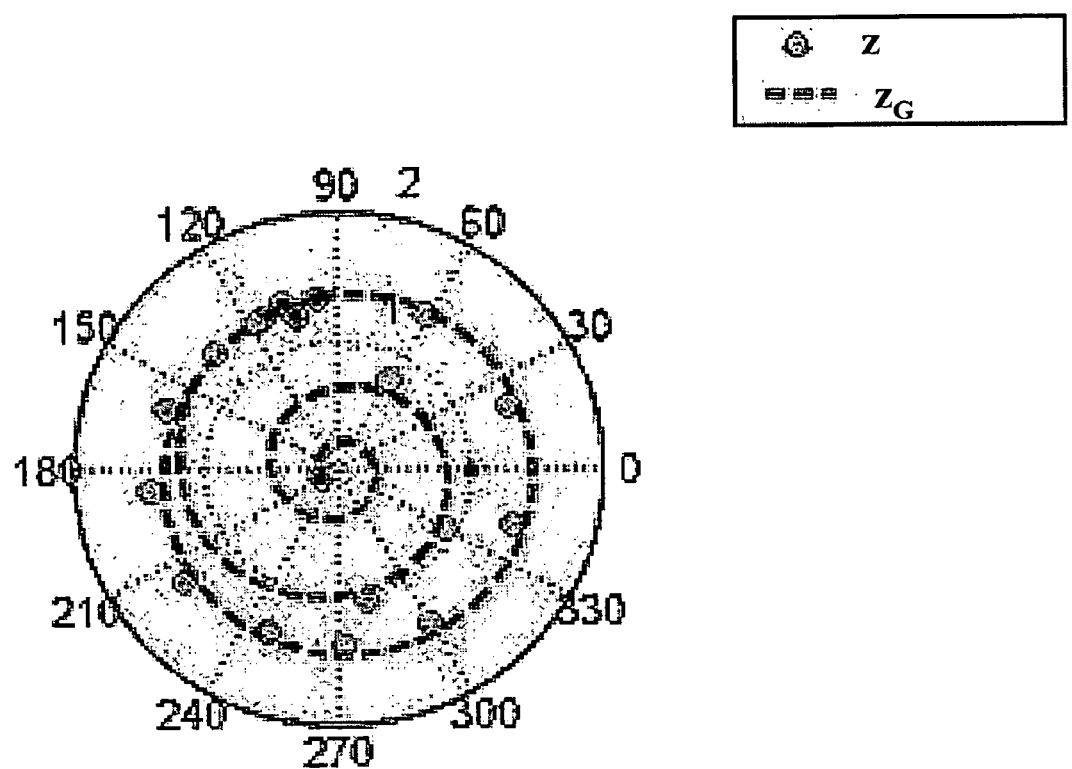
FIG. 5 shows, in a polar diagram, the attenuation and phase shift pairs of microwave beams that have traversed a medium

FIG. 5 shows, in a polar diagram, the attenuation and phase shift pairs of a microwave beam that has traversed a water/oil mixture. The dots designate the measured attenuation and phase shift pairs z. The spiral dotted line represents the attenuation and phase shift pairs $z_G$ obtained by the measurement model.

In F, the proportion of oil $\alpha_{oil}$, of gas $\alpha_{gas}$ and of water $\alpha_{water}$ is determined by seeking the proportions of oil, gas and water which minimize the sum, on the different measurement frequencies f, of the distance (or norm) between, on the one hand, the measured attenuation and phase shift pair z and, on the other hand, the attenuation and phase shift pair $z_G$ given by the measurement model valid for the measuring frequency f.

For example, the following mathematical relation can be applied:

$$(\hat{\alpha}_e, \hat{\alpha}_g) = \underset{(\alpha e, \alpha g)}{\operatorname{argmin}} \left\{ \sum_{nf} |z_f - z_{G_f}(\alpha e, \alpha g)|^2 \right\}$$

For example, if three attenuation and phase shift measurements are performed at three microwave frequency values fa, fb and fc, the proportions of oil, gas and water are determined by seeking the proportions of water and of gas that minimize the sum of the following distances: the distance between the attenuation and phase shift pair z measured at frequency fa and the attenuation and phase shift pair $z_G$ given by the measurement model valid for frequency fa, the distance between the attenuation and phase shift pair z measured at frequency fb and the attenuation and phase shift pair $z_G$ given by the measurement model valid for frequency fb, and the distance between the attenuation and phase shift pair z measured at frequency fc and the attenuation and phase shift pair $z_G$ given by the measurement model valid for frequency fc.

More precisely, when using measurement models $z_{GOR}(\alpha_e)$ (with $$\alpha_{GOR} = \frac{\alpha_g}{\alpha_h + \alpha_g}$$

constant) and $z_{WC}(\alpha_g)$ (with $$\alpha_{WC} = \frac{\alpha_e}{\alpha_h + \alpha_e}$$

constant) previously determined for a petroleum effluent, the proportion of gas $\alpha_g$ and of water $\alpha_e$ can be determined by minimizing the distances between the measurement and the model for each one of the two models.

For example, the following relation can be applied:

$$(\hat{\alpha}_{water}, \hat{\alpha}_{gas}) = \arg_{M \in \Delta} \min \{J_{GOR}(\alpha_{water})^2 + J_{WC}(\alpha_{gas})^2\}$$

$$\hat{\alpha}_{oil} = 1 - \hat{\alpha}_{water} - \hat{\alpha}_{gas}$$

with $$\begin{cases} J_{GOR}(\alpha_{water}) = \sum_{nf} |z_f - z_{GOR_f}(\alpha_{water}, T, \text{Salt}, \varepsilon_{GOR})|^2 \\ J_{WC}(\alpha_{gas}) = \sum_{nf} |z_f - z_{WC_f}(\alpha_{gas}, T, \text{Salt}, \varepsilon_{WC})|^2 \end{cases}$$

It is also possible to use, without departing from the scope of the invention, other physical models modelling, on the one hand, the permittivity of a fluid resulting from mixing several phases of known permittivity and, on the other hand, the propagation of a microwave beam through a multiphase fluid.

The invention claimed is:

1. A method of determining the composition of a multiphase fluid comprising at least two mixed phases, comprising:
   a) selecting a mixture law that expresses a mean permittivity of the fluid as a function of permittivity and volume fraction of each phase;
   b) measuring an attenuation and a phase shift of at least two microwave beams of different frequencies that have traversed test fluids of known composition;
   c) from the mixture law and from the attenuation and phase shift measurements performed in b), determining for each one of the frequencies a measurement model that expresses the attenuation and the phase shift of a microwave beam as a function of the volume fraction of each phase;
   d) for each one of the frequencies, measuring an attenuation and a phase shift pair for at least one microwave beam that has traversed said multiphase fluid;
   e) determining the composition of the multiphase fluid by determining a value of volume fractions of the phases that minimize a function taking accounting for the distances, calculated for each one of the frequencies, between a point whose coordinates correspond to an attenuation and the phase shift pair measured for a value of the frequencies and a point whose coordinates correspond to the attenuation and phase shift pair determined by one of the models valid for the same frequency value.

2. A method as claimed in claim 1 wherein, in e), the function is a sum of the distances.

3. A method as claimed in claim 2 wherein, in e), a value of the volume fractions that minimizes a sum of the at least two following distances is determined: a distance between an attenuation and a phase shift pair measured for a first one of the frequencies and an attenuation and a phase shift pair determined by one of the models valid for a first one of the frequencies, and a distance between an attenuation and a phase shift pair measured for a second one of the frequencies and an attenuation and a phase shift pair determined by another one of the models valid for the second one of the frequencies.

4. A method as claimed in claim 2, wherein the fluid is a petroleum effluent comprising water, oil and gas, wherein, in c), a first measurement model expressing an attenuation and a phase shift of a microwave beam as a function of the volume fraction of water is determined and a second measurement model expressing an attenuation and a phase shift of a microwave beam as a function of a volume fraction of gas is determined, and wherein, in e), a value of a volume fraction of water minimizing the sums, on the frequencies, of the distances between the measured attenuation and phase shift pair and the attenuation and the phase shift pair determined by the first model is determined, and a value of the volume fraction of gas minimizing the sums, on the frequencies, of the distances between the measured attenuation and the phase shift pair and the attenuation and the phase shift pair determined by the second model is determined.

5. A method as claimed in claim 1 wherein, in a), a mixture law is selected from among the Bruggeman-Hanaï law, a Tinga-Voss-Blossey law and a law given by a CRIM method.

6. A method as claimed in claim 4, wherein the first model is determined from the Bruggeman-Hanaï law and the second model is determined from a law given by the CRIM method.

7. A method as claimed in claim 1 wherein, before a), permittivity values of the phases are determined and the permittivity values are used in a).

8. A method as claimed in claim 1 wherein, in b), microwave beams of frequencies included in the range from 2 GHz to 10 GHz are used.

9. A method as claimed in claim 1 wherein, in b), attenuation and phase shift measurements are performed at one microwave frequency and a mean of the measurements is determined.

10. A method as claimed in claim 1, wherein the fluid is a petroleum effluent including of gas, oil and water.

11. A method as claimed in claim 3, wherein the fluid is a petroleum effluent comprising water, oil and gas, wherein, in c), a first measurement model expressing an attenuation and a phase shift of a microwave beam as a function of the volume fraction of water is determined and a second measurement model expressing an attenuation and a phase shift of a microwave beam as a function of a volume fraction of gas is determined, and wherein, in e), a value of a volume fraction of water minimizing the sums, on the frequencies, of the distances between the measured attenuation and phase shift pair and the attenuation and the phase shift pair determined by the first model is determined, and a value of the volume fraction of gas minimizing the sums, on the frequencies, of the distances between the measured attenuation and the phase shift pair and the attenuation and the phase shift pair determined by the second model is determined.

12. A method as claimed in claim 2 wherein, in a), a mixture law is selected from among the Bruggeman-Hanaï law, a Tinga-Voss-Blossey law and a law given by a CRIM method.

13. A method as claimed in claim 3 wherein, in a), a mixture law is selected from among the Bruggeman-Hanaï law, a Tinga-Voss-Blossey law and a law given by a CRIM method.

14. A method as claimed in claim 4 wherein, in a), a mixture law is
   selected from among the Bruggeman-Hanaï law, a Tinga-Voss-Blossey law and a law given by a CRIM method.

15. A method as claimed in claim 2 wherein, before a), permittivity values of the phases are determined and the permittivity values are used in a).

16. A method as claimed in claim 3 wherein, before a), permittivity values of the phases are determined and the permittivity values are used in a).

17. A method as claimed in claim 4 wherein, before a), permittivity values of the phases are determined and the permittivity values are used in a).

18. A method as claimed in claim 5 wherein, before a), permittivity values of the phases are determined and the permittivity values are used in a).

19. A method as claimed in claim 6 wherein, before a), permittivity values of the phases are determined and the permittivity values are used in a).

20. A method as claimed in claim 2 wherein, in b), microwave beams of frequencies included in the range from 2 GHz to 10 GHz are used.

21. A method as claimed in claim 3 wherein, in b), microwave beams of frequencies included in the range from 2 GHz to 10 GHz are used.

22. A method as claimed in claim 4 wherein, in b), microwave beams of frequencies included in the range from 2 GHz to 10 GHz are used.

23. A method as claimed in claim 5 wherein, in b), microwave beams of frequencies included in the range from 2 GHz to 10 GHz are used.

24. A method as claimed in claim 6 wherein, in b), microwave beams of frequencies included in the range from 2 GHz to 10 GHz are used.

25. A method as claimed in claim 7 wherein, in b), microwave beams of frequencies included in the range from 2 GHz to 10 GHz are used.

26. A method as claimed in claim 2 wherein, in b), attenuation and phase shift measurements are performed at one microwave frequency and a mean of the measurements is determined.

27. A method as claimed in claim 3 wherein, in b), attenuation and phase shift measurements are performed at one microwave frequency and a mean of the measurements is determined.

28. A method as claimed in claim 4 wherein, in b), attenuation and phase shift measurements are performed at one microwave frequency and a mean of the measurements is determined.

29. A method as claimed in claim 5 wherein, in b), attenuation and phase shift measurements are performed at one microwave frequency and a mean of the measurements is determined.

30. A method as claimed in claim 6 wherein, in b), attenuation and phase shift measurements are performed at one microwave frequency and a mean of the measurements is determined.

31. A method as claimed in claim 7 wherein, in b), attenuation and phase shift measurements are performed at one microwave frequency and a mean of the measurements is determined.

32. A method as claimed in claim 8 wherein, in b), attenuation and phase shift measurements are performed at one microwave frequency and a mean of the measurements is determined.

* * * * *